United States Patent
Wiedekind-Klein

(10) Patent No.: US 9,863,905 B2
(45) Date of Patent: Jan. 9, 2018

(54) METHOD FOR DETECTING CONTACT OF A PIPETTING NEEDLE

(71) Applicant: Siemens Healthcare Diagnostics Products GmbH, Marburg (DE)

(72) Inventor: Alexander Wiedekind-Klein, Cochem (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 0 days.

(21) Appl. No.: 15/199,970

(22) Filed: Jun. 30, 2016

(65) Prior Publication Data
US 2017/0003242 A1 Jan. 5, 2017

(30) Foreign Application Priority Data

Jul. 3, 2015 (EP) .................................. 15175186

(51) Int. Cl.
*G01N 27/22* (2006.01)
*G01N 33/487* (2006.01)
*G01N 35/10* (2006.01)

(52) U.S. Cl.
CPC ..... *G01N 27/228* (2013.01); *G01N 33/48785* (2013.01); *G01N 35/1011* (2013.01);
(Continued)

(58) Field of Classification Search
CPC ......... G01N 2035/1034; G01N 27/228; G01N 33/48785; G01N 35/1011
USPC ...... 324/500, 677–688, 600, 755.11, 756.04, 324/76.11, 76.32, 76.34, 76.65–76.76, 89, 324/122
See application file for complete search history.

(56) References Cited

U.S. PATENT DOCUMENTS 4,326,851 A 4/1982 Keine
5,365,783 A 11/1994 Keine
(Continued)

FOREIGN PATENT DOCUMENTS

| AU | 2005211570 | 10/2005 |
| DE | 10 2006 05283 | 5/2008 |
| EP | 0913671 | 5/1999 |

OTHER PUBLICATIONS

European Search Report of European Application No. 15175186.4-1405 dated Dec. 21, 2015.

*Primary Examiner* — Melissa Koval
*Assistant Examiner* — Trung Nguyen
(74) *Attorney, Agent, or Firm* — Dugan & Dugan, PC

(57) ABSTRACT

The invention relates to a method for detecting contact of a pipetting needle in an in vitro diagnostic system. To this end, the pipetting needle, in an advantageous embodiment of the invention, should be cyclically charged by an electric voltage or current applied between the pipetting needle and a reference potential and discharged again by a subsequent electric connection between the pipetting needle and the reference potential. A characteristic variable for the current capacitance between the pipetting needle and the reference potential should be established from a number of measured values detected during the charging and/or discharging. A temporal curve of the characteristic variable should be monitored continuously based on a number of predetermined criteria and a contact signal should be generated if the predetermined criteria are satisfied.

15 Claims, 3 Drawing Sheets

(52) U.S. Cl.
CPC ........... *G01N 2035/1025* (2013.01); *G01N 2035/1032* (2013.01); *G01N 2035/1034* (2013.01)

(56) References Cited

U.S. PATENT DOCUMENTS

| | | |
|---|---|---|
| 5,648,727 A | 7/1997 | Keine |
| 8,277,756 B2 | 10/2012 | Gorka |
| 2006/0093525 A1* | 5/2006 | Brunner ............ G01F 23/2965 422/509 |
| 2014/0152326 A1* | 6/2014 | Zuppiger ........... G01N 35/1011 324/663 |

* cited by examiner

METHOD FOR DETECTING CONTACT OF A PIPETTING NEEDLE

CROSS REFERENCE TO RELATED APPLICATION

This claims priority to European Patent Application No. EP 15175186.4, filed Jul. 3, 2015, which is hereby incorporated by reference herein in its entirety for all purposes.

FIELD

The invention relates to a method for detecting contact of a pipetting needle in an in vitro diagnostic system.

BACKGROUND

These days, several detection and analysis methods for determining physiological parameters in bodily fluid samples or in biological samples are carried out in large numbers in an automated manner in corresponding in vitro diagnostic systems. To this end, use is made of vessels referred to as cuvettes, which are suitable for samples, reagents and also the actual detection reaction. The blood samples are supplied to the device in blood sample tubes.

Blood sample tubes are usually manufactured from transparent plastic or glass and equipped at the tip thereof with a special connector for cannulas.

Current in vitro diagnostic systems are able to carry out a multiplicity of detection reactions and analyses using one sample. To this end, such devices usually comprise a receptacle position for a reaction vessel and an analysis system associated with the receptacle position. In order to be able to carry out a multiplicity of examinations in an automated manner, it is necessary to take small amounts of liquid from the corresponding containers by way of automated pipetting at a number of points. Thus, for example, aliquots of the blood sample must be taken from the blood sample tubes or exactly predetermined portions of reagents must be taken from the reagent containers and transferred into the reaction vessel provided for the respective examination. To this end, a plurality of appropriate pipetting systems are provided in the system, depending on usage purpose.

Such a pipetting system usually has a pipetting needle at an actively movable element, such as, e.g., a transport arm or swivel arm, which pipetting needle is fastened in a needle holder on the pipetting arm. The pipetting needle is configured as a hollow needle which is able to take defined amounts of sample in an automated manner under operation with pressure or negative pressure, with and without control liquids. The pipetting needle is inserted along the central axis of the respective vessel, penetrates an elastic sealing plug in the case of sealed vessels when necessary and is immersed into the liquid. The immersion, i.e., the contact with the liquid surface, is detected by means of an appropriate contact detection apparatus and the predetermined amount is sucked in under pressure control. The removed amount is then supplied to the appropriate analysis. Subsequently, the pipetting needle is rinsed in an appropriate apparatus and it is available for the next use.

In the above-described process, the reliable identification of contact with the surface of the liquid is mandatory in order, firstly, to determine the fill level of the liquid and, secondly, to ensure that no air is pipetted. What is problematic in this case is that the amounts of liquid to be detected are very small (in part a few µL), and so known techniques of fill level measurement, such, as e.g., by way of floats, inductivity or conductivity, are hardly usable.

Therefore, in the past, in vitro diagnostic systems have generally used a capacitive measurement, which was realized as purely analog switching technology on the basis of operational amplifiers. The necessary sensitivity could only be achieved by the detection of changes in capacitance, which were then reported to the control electronics by a voltage pulse.

A disadvantage here is that occurring disturbances, such as, e.g., electrostatic discharges and radio frequency fields, may likewise generate such voltage pulses. Therefore, there has been no possibility until now of distinguishing between disturbance and real voltage pulse as a contact signal in known systems.

SUMMARY

It is therefore an object of the invention to specify a method of the type set forth at the outset, which enables a more reliable determination of contact by the pipetting needle and which is particularly insensitive to disturbances.

According to the invention, this object is achieved by virtue of:
 the pipetting needle being cyclically charged by an electric voltage or current applied between pipetting needle and a reference potential and discharged again by a subsequent electric connection between the pipetting needle and the reference potential,
 a characteristic variable for the current capacitance between pipetting needle and reference potential being established from a number of measurement variables detected during the charging and/or discharging, and
 the temporal curve of the variable being monitored continuously on the basis of a number of predetermined criteria and a contact signal being generated if the predetermined criteria are satisfied.

Here, the invention proceeds from the idea that a more reliable detection of contact could be achieved by virtue of a continuous absolute capacitive measurement being carried out instead of only a point-by-point relative measurement. This is achievable in a particularly simple manner by virtue of the capacitance between pipetting needle and the surroundings thereof, which constitute a reference potential (e.g. the ground or housing potential), being used as a reference variable. By considering measured values during cyclical charging and discharging processes of the pipetting needle, it is possible to establish a suitable variable which is characteristic for the current capacitance between pipetting needle and reference potential as the charge transferred with a predetermined voltage or current during the charging process is dependent on the capacitance. This variable, which represents the capacitance between the pipetting needle and the surroundings thereof, can be used as a base variable for continuous monitoring and it is possible to predetermine suitable criteria for detecting contact. This is because, for the application in the field of fill-level detection, a calibration of the circuit to an absolute variable in farad is not necessary.

However, by way of example, the variable characteristic for the capacitance likewise can be the capacitance itself, which is, e.g., specified in the SI unit farad.

Here, one of the predetermined criteria is advantageously specified by the variable being increased by a minimum value within a predetermined period of time. This is because the measured capacitance increases when the pipetting needle is immersed. This increase of the variable characterizing the capacitance can be identified by pre-determining an increase within a specific period of time. This specific, predetermined period of time is advantageously less than 10 ms, in particular less than 5 ms. This is because the change in the capacitance is jump-like upon immersion into the liquid such that a significant increase in the capacitance is measurable within this short period of time.

In respect of the height of this jump in the capacitance, a fixed minimum value can advantageously be specified within the scope of the method. By way of example, said minimum value can be determined in advance on the basis of trial measurements.

However, in an alternative advantageous refinement of the method, the minimum value can also be determined dynamically in a manner dependent on the strength of a noise of the variable characteristic for the capacitance. By way of example, it can correspond to a factor of the strength of the basic noise of the variable or of the amount of liquid to be expected.

Furthermore, an additional criterion for detecting the contact with the liquid surface is advantageously provided by virtue of the variable remaining constant within a range for a second predetermined period of time following the predetermined period of time in time. This is because, in addition to the jump upon contact with the surface, the capacitance curve is characterized by the value remaining the new value after the jump. To this end, a value window with an upper and lower deviation can be predetermined, with the value having to remain within the scope thereof for a specific period of time.

This second predetermined period of time of remaining is advantageously longer than 10 ms. As a result of this, it is possible to exclude the case, in particular, where the contact detection erroneously responds to a jump caused, e.g., by electromagnetic disturbance signals as such signals generally endure for a shorter period of time.

In a first advantageous refinement, a fixed range can be predetermined for the aforementioned value window in a manner analogous to the jump height. Said range can in turn be determined in advance by way of test measurements.

Alternatively, the range can advantageously likewise be determined dynamically in a manner dependent on the strength of a noise of the variable characteristic for the capacitance or on the amount of liquid to be expected.

In order to minimize the influence of the noise when establishing the variable characteristic for the capacitance, a time average value is advantageously formed when establishing said variable. As a result of this, short-term jumps caused by noise are equalized.

A further advantage of the above-described absolute capacitance measurement compared to the prior art lies in the possibility of detecting additional errors, which are not directly related to the detection of surfaces. To this end, an error signal is advantageously output if a predetermined first reference value of the variable is undershot and/or if a predetermined second reference value of the variable is exceeded. This is because the pipetting needle is not present or not correctly connected if the capacitive rest value is too small when compared to a known reference value. If the capacitive rest value is too large compared to a known reference value, the pipetting needle is defective or contacts a conductive surface.

Different measurement variables substantially linked to the charge transferred during the charging and discharging can be used as a variable characteristic for the capacitance. However, a refinement of the method which is particularly simple to realize emerges by virtue of using the number of charging and discharging processes within a predetermined period of time as a variable. The greater the capacitance, the longer the charging process up to a predetermined voltage takes.

Establishing this variable is advantageously achieved in a particularly simple manner by virtue of the charging being carried out by means of a constant current source, discharging being started once a predetermined voltage is reached and a new cycle being started with renewed charging after reaching a zero voltage. To this end, provision can be made of a comparator within the electric circuit responsible therefor.

A contact detection apparatus for an in vitro diagnostic system is advantageously embodied to carry out the method described.

An in vitro diagnostic system advantageously comprises such a contact detection apparatus.

The advantages obtained by means of the invention consist of, in particular, error signals as a result of electromagnetic disturbances largely being eliminated by way of a contact detection on the basis of the absolute capacitance between pipetting needle and a reference potential and, as a result thereof, more reliable pipetting being possible in an in vitro diagnostic system. This approach moreover makes it possible to dispense with a special measuring electrode since the pipetting needle used for the liquid transport can be used directly. Furthermore, error states such as a disconnected needle or contact with a conductive surface can be reliably identified. By way of example, this can also be used for adjusting movable parts (e.g., transport arms).

BRIEF DESCRIPTION OF THE DRAWINGS

An exemplary embodiment of the invention is explained in more detail on the basis of a drawing. Therein.

In all figures, the same parts are provided with the same reference signs.

DETAILED DESCRIPTION

Figure 1:
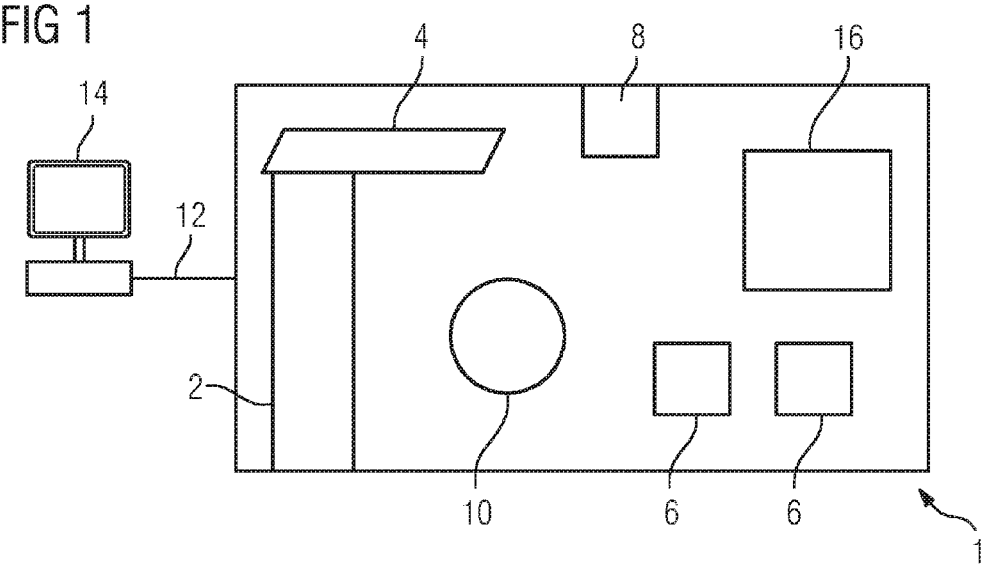
FIG. 1 shows a schematic illustration of an in vitro diagnostic system.

FIG. 1 shows a schematic illustration of an in vitro diagnostic system 1 with some of the components contained therein. Here, only the most important components are shown in a much simplified manner so as to explain the basic functionality of the in vitro diagnostic system 1, without depicting the individual parts of each component in great detail here.

The in vitro diagnostic system 1 is embodied to carry out very different types of analysis of blood or other bodily fluids in a fully automatic manner, without activities of a user being necessary herefor. Instead, said activities are restricted to servicing or repair and refilling work, for example if cuvettes or reagents need to be refilled.

In the in vitro diagnostic system 1, the samples are supplied on sleds (not depicted in any more detail here) in a supply rail 2. In this case, information in respect of the analyses to be carried out per sample can be transferred by means of e.g. barcodes applied to the sample vessels, said barcodes being read in the in vitro diagnostic system 1. Aliquots are taken from the samples in a pipetting apparatus 4 by means of a pipetting needle yet to be depicted in more detail in FIG. 2.

The aliquots are likewise supplied to cuvettes (not depicted in any more detail here), in which the actual analyses are carried out by means of very different measuring instruments 6, such as, e.g., photometers. The cuvettes are taken from a cuvette storage 8. Additionally, further reagents, which are required depending on the analysis to be carried out, can be supplied to the respective cuvette from a reagent storage 10 by means of a further pipetting needle which, as already mentioned above, is depicted in FIG. 2.

Within the in vitro diagnostic system, the cuvettes are transported by means of transport apparatuses (not depicted in any more detail here) such as, e.g., transfer arms, which are movable in very different spatial directions and which have a gripper apparatus for holding the cuvettes. The entire process is controlled by means of a control apparatus, such as, e.g., a computer 14 connected by way of a data line 12, supported by a multiplicity of further electronic circuits (not depicted in any more detail here) and microprocessors within the in vitro diagnostic system 1 and the components thereof.

Figure 2:
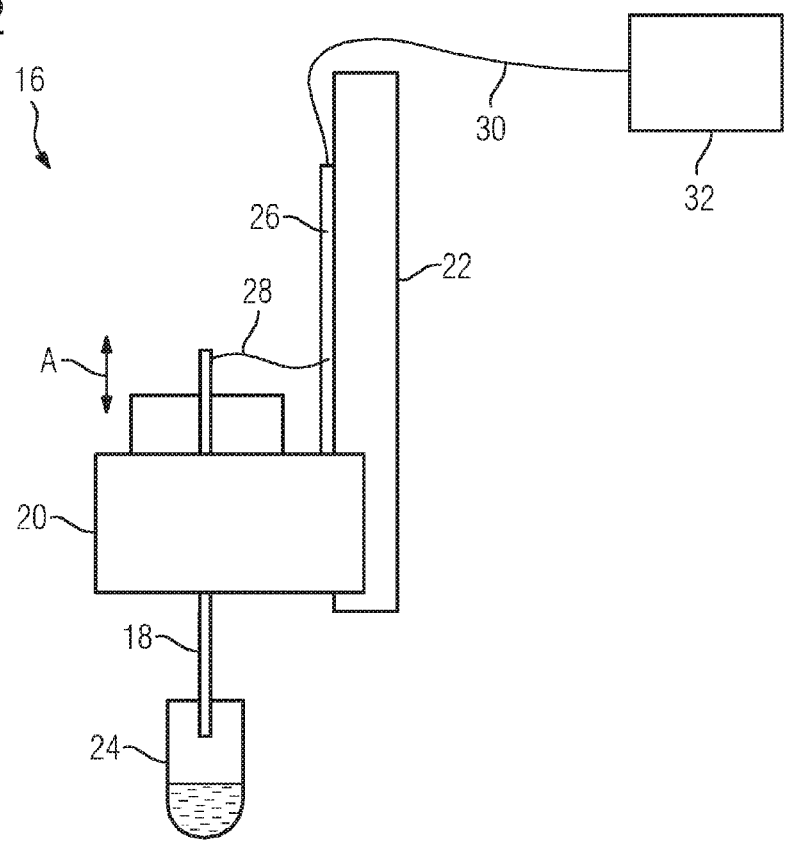
FIG. 2 shows a schematic illustration of a pipetting needle fastened to a transport arm in the in vitro diagnostic system.

FIG. 2 schematically shows one of the pipetting devices 16 with a pipetting needle 18 present in the in vitro diagnostic system 1. The pipetting needle 18 is fastened to a transfer arm 22 by means of a holder 20 and movable in an automated manner along the axis of the pipetting needle 18, at least in the movement direction A, in order to be able to be inserted into a vessel 24 with a liquid and in order to pipette the liquid.

In order to detect contact with the liquid surface during pipetting, the in vitro diagnostic system 1 comprises a contact detection apparatus, which initially has a printed circuit board 26 with an electric circuit, which, as a result, enables absolute capacitance measurements in the upper femtofarad or lower picofarad range and which is described below:

The electric circuit of the printed circuit board 26 comprises a constant current source which, by way of an electric connection 28, can apply a charge onto the pipetting needle 18. In relation to the ground zero level, which is used as a reference potential, the pipetting needle 18 forms a capacitance to be measured, which is therefore charged. Furthermore, the electric circuit has a resistor, by means of which the capacitance can be discharged again, i.e., the charge can be dissipated from the pipetting needle 18 again by way of the electric connection 28. Furthermore, the electric circuit has a comparator which signals the charge state and therefore, in particular, is able to indicate a specific voltage between pipetting needle 18 and ground zero level being reached.

A digital controller now continuously carries out many cyclical charging and discharging processes, each process only having a duration of 1-10 μs. Here, the pipetting needle 18 is charged until a certain voltage value is reached, and it is discharged again when the voltage value is reached, until a zero voltage is reached. Then, a new charging process starts. In one embodiment, the printed circuit board 26 forwards a signal for each charging process to a control apparatus 32 by way of the connection 30. However, in the embodiment described in more detail below, the printed circuit board 26, as an integrated circuit, evaluates the whole capacitance measurement with counting, etc., and only forwards the result, i.e., the magnitude of the capacitance, to the control apparatus 32. The control apparatus 32 can be the computer 14 from FIG. 1 or else it can be an upstream specific circuit as a control apparatus 32 in the form of an integrated circuit which is integrated into the in vitro diagnostic system 1.

The circuit on the printed circuit board 26 controls and evaluates the charging and discharging processes. The length of the charging process increases with increasing capacitance between pipetting needle 18 and ground zero level. Hence, the number of charging and discharging processes taking place per unit time is a variable characteristic for the absolute capacitance. By way of forming an average value which, for example, is carried out in a processor part, the circuit on the printed circuit board 26 determines measured values of the variable which represents the capacitance. These measured values are unitless numerical values which characterize the measured capacitance. In FIGS. 3 to 6, these numerical values are plotted over time in ms. For application in the field of detecting contact with the liquid level, there is no need to calibrate the circuit to an absolute value in farad.

In the control apparatus 32, the contact is detected by means of an evaluation algorithm which uses signals supplied by way of the connection 30. Here, the evaluation algorithm analyzes the curve of the variable characteristic for the capacitance value of the pipetting needle 18 and analyzes the latter according to various aspects, such as absolute value, rate of changes, gradient of the changes and continuity of the changes. Curves of this variable are plotted as a graph over time in FIGS. 3 to 6.

Figure 3:
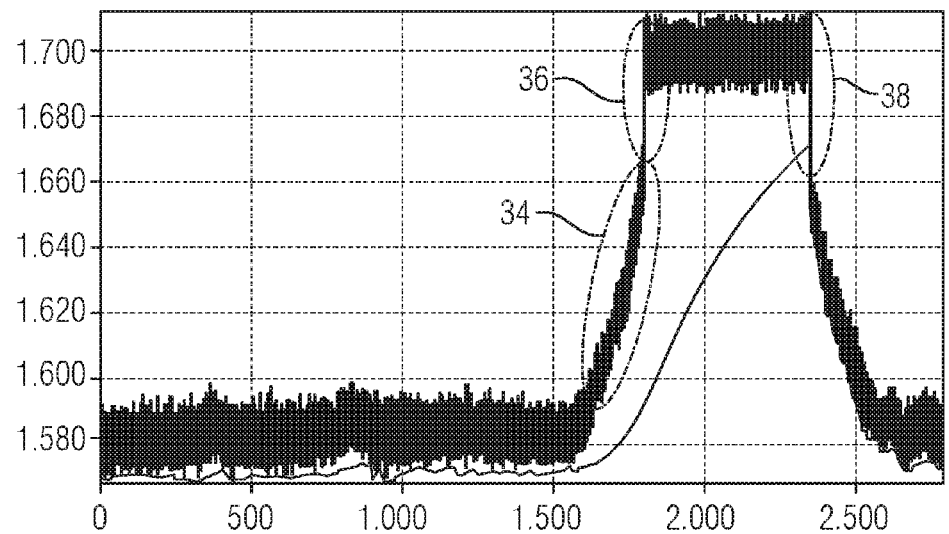
FIG. 3 shows a graph of the curve of the variable characteristic for the capacitance during the immersing and emerging process of the pipetting needle.
Figure 4:
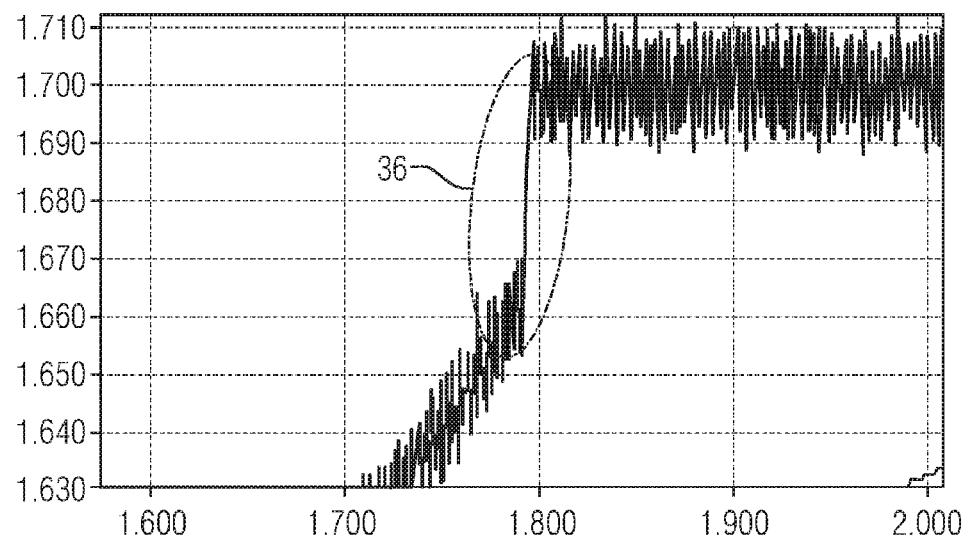
FIG. 4 shows a sectional magnification of the graph from FIG. 3.

The fundamental principle of this algorithm is the fact that the measured capacitance increases upon immersion of the needle or upon contact with a conductive surface. FIG. 3 shows how the capacitance signal behaves upon immersion in a sample tube (uniform increase in region 34) and the subsequent contact with the liquid surface (jump-like change in region 36). Region 36 is depicted in a magnified manner in FIG. 4. The superposed signal noise is also readily identifiable; however, it does not impair the evaluability of the used signals.

At the instant of contact in region 36, the capacitance changes in a jump-like manner and then remains at the new value. Naturally, this process also applies in reverse, when the liquid is left or the contact ends (see region 38 in FIG. 3). To this end, the algorithm evaluates the curve of the variable. Here, it seeks points of discontinuity, i.e., regions in which the variable increases beyond a predetermined minimum value within a short period of time of less than 1 ms, and furthermore monitors whether, and how long for, the new signal level remains. To this end, provision is made in one embodiment for the curve having to stay within a specific range within a period of more than 10 ms. The strength of the signal noise can be included dynamically when setting minimum values and ranges. Alternatively, it is possible to predetermine fixed values.

Figure 5:
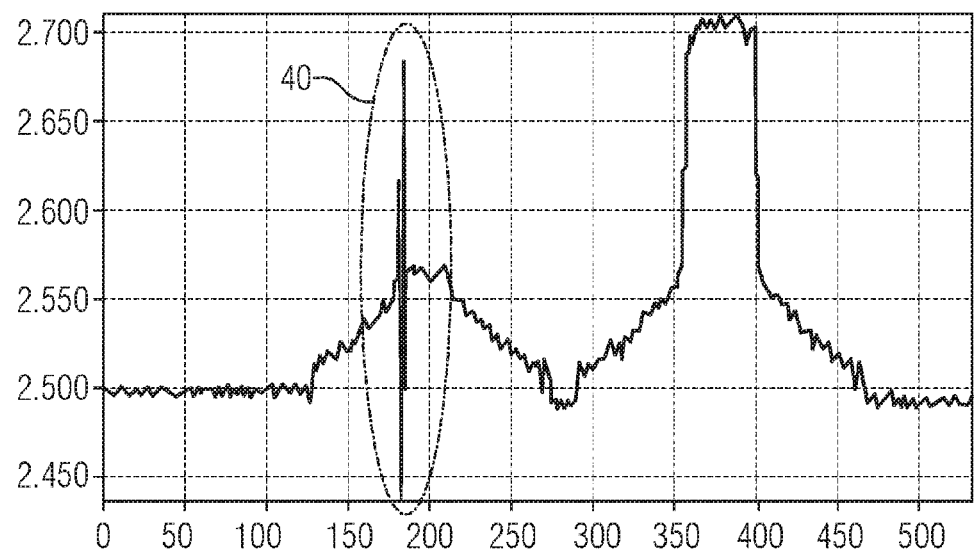
FIG. 5 shows a graph of the curve of the variable characteristic for the capacitance in the case of an electromagnetic disturbance signal.
Figure 6:
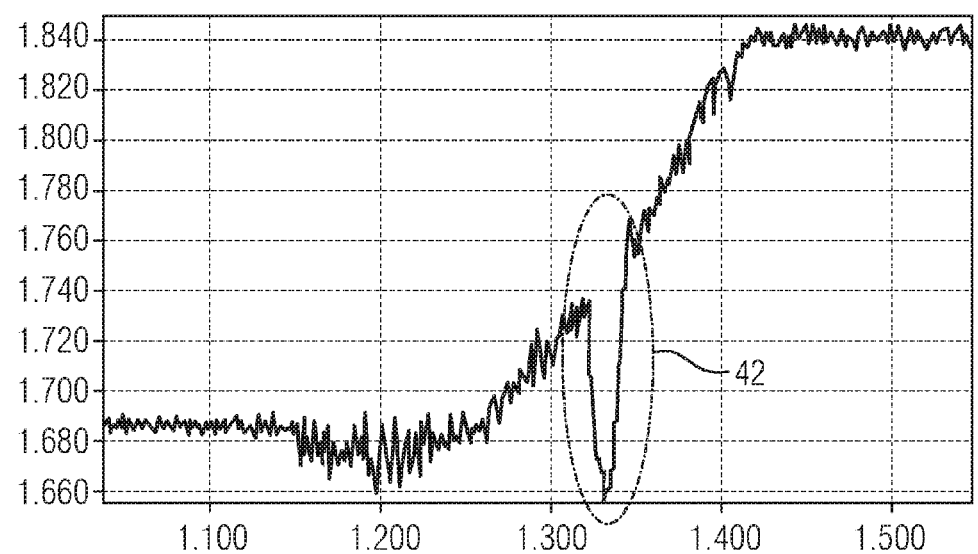
FIG. 6 shows a graph of the curve of the variable characteristic for the capacitance in the case of a disturbance in the continuity, for example due to a loose connection.

A disturbance can be distinguished from a correct contact with the surface of the liquid with the aid of the algorithm. FIGS. 5 and 6 show two typical disturbance scenarios. In region 40, FIG. 5 shows a point-like superelevation of the noise amplitude by an electromagnetic disturbance. In region 42, FIG. 6 shows a brief drop in the curve of the variable, for example due to a loose contact. However, these signals are not misinterpreted as contact signals due to the short duration. It is readily possible to identify that the used signals also remain evaluable in this case. Both cases would lead to erroneous measurements using the prior art (pure detection of changes in capacitance).

A further function of the algorithm is not depicted in any more detail: reference values are predetermined, with an error signal being output in each case if said reference values are exceeded or undershot: this is because the pipetting needle 18 is not present or incorrectly connected if the capacitive rest value is too small when compared to a known reference value. If the capacitive rest value is too large when compared to a known reference value, the pipetting needle 18 is defective or in contact with a conductive surface. The latter signals can also be used for adjusting the pipetting needle 18.

LIST OF REFERENCES

1 In vitro diagnostic system
2 Supply rail
4 Pipetting apparatus
6 Measuring instrument
8 Cuvette storage
10 Reagent storage
12 Data line
14 Computer
16 Pipetting device
18 Pipetting needle
20 Holder
22 Transfer arm
24 Vessel
26 Printed circuit board
28 Electric connection
30 Connection
32 Control apparatus
34,36,38,40,42 Regions of capacitive signal curves
A Movement direction

What is claimed is:

1. A method for detecting contact of a pipetting needle in an in vitro diagnostic system, the method comprising:
    cyclically charging the pipetting needle by an electric voltage or current applied between the pipetting needle and a reference potential and cyclically discharging by a subsequent electric connection between the pipetting needle and the reference potential,
    establishing a characteristic variable for a current capacitance between the pipetting needle and the reference potential from a number of measured values detected during the charging and discharging, and
    monitoring continuously a temporal curve of the characteristic variable based on a number of predetermined criteria and generating a contact signal if the predetermined criteria are satisfied;
    wherein a number of charging and discharging processes within a predetermined period of time is used as the characteristic variable for the current capacitance between the pipetting needle and the reference potential.

2. The method as claimed in claim 1, wherein a predetermined criterion is given by the characteristic variable being increased by a minimum value within a first predetermined period of time.

3. The method as claimed in claim 2, wherein the predetermined period of time is less than 10 ms.

4. The method as claimed in claim 2, wherein a fixed minimum value is predetermined.

5. The method as claimed in claim 2, wherein the minimum value is determined in a manner dependent on a strength of a noise of the characteristic variable.

6. The method as claimed in claim 2, wherein an additional criterion is given by the characteristic variable remaining constant within a range for a second predetermined period of time following the first predetermined period of time.

7. The method as claimed in claim 6, wherein the second predetermined period of time is more than 10 ms.

8. The method as claimed in claim 6, wherein a fixed range is predetermined.

9. The method as claimed in claim 6, wherein the range is determined in a manner dependent on a strength of a noise of the characteristic variable.

10. The method as claimed in claim 2, wherein the predetermined period of time is less than 5 ms.

11. The method as claimed in claim 1, wherein a time average value is formed when establishing the characteristic variable.

12. The method as claimed in claim 1, wherein an error signal is output if a predetermined first reference value of the characteristic variable is undershot or if a predetermined second reference value of the characteristic variable is exceeded.

13. The method as claimed in claim 1, wherein charging is carried out via a constant current source, discharging is started once a predetermined voltage is reached and a new cycle is started with renewed charging after reaching a zero voltage.

14. A contact detection apparatus for an in vitro diagnostic system, comprising a constant current source, a pipetting needle, a resistor and a comparator, wherein the contact detection apparatus is embodied to carry out the method as claimed in claim 1.

15. An in vitro diagnostic system comprising the contact detection apparatus as claimed in claim 14.

* * * * *